(12) United States Patent
Chen

(10) Patent No.: US 6,555,722 B2
(45) Date of Patent: Apr. 29, 2003

(54) COUNTERCURRENT ALKYLATION PROCESS

(75) Inventor: Jamin Chen, Houston, TX (US)

(73) Assignee: Catalytic Distillation Technologies, Pasadena, TX (US)

(*) Notice: Subject to any disclaimer, the term of this patent is extended or adjusted under 35 U.S.C. 154(b) by 7 days.

(21) Appl. No.: 10/098,100

(22) Filed: Mar. 13, 2002

(65) Prior Publication Data

US 2002/0128529 A1 Sep. 12, 2002

Related U.S. Application Data

(63) Continuation of application No. 09/445,783, filed as application No. PCT/US97/12710 on Jul. 16, 1997.

(51) Int. Cl.$^7$ .................................................. C07C 2/68
(52) U.S. Cl. ........................ 585/467; 585/447; 585/449; 203/DIG. 6
(58) Field of Search ................. 585/447, 449, 585/467; 203/DIG. 6

(56) References Cited

U.S. PATENT DOCUMENTS

| | | | |
|---|---|---|---|
| 4,469,908 A | 9/1984 | Burress | 585/467 |
| 4,891,458 A | 1/1990 | Innes et al. | 585/323 |
| 4,950,834 A | 8/1990 | Arganbright et al. | 585/446 |
| 5,019,669 A | 5/1991 | Adams et al. | 585/446 |
| 5,030,786 A | 7/1991 | Shamshoum et al. | 585/467 |
| 5,081,323 A | 1/1992 | Innes et al. | 585/449 |
| 5,082,990 A * | 1/1992 | Hsieh et al. | 208/46 |
| 5,113,031 A | 5/1992 | Sy | 585/467 |
| 5,118,896 A | 6/1992 | Steigelmann et al. | 585/467 |
| 5,196,623 A | 3/1993 | Butler | 585/467 |
| 5,215,725 A | 6/1993 | Sy | 422/212 |
| 5,243,115 A | 9/1993 | Smith, Jr. et al. | 585/446 |

* cited by examiner

Primary Examiner—Thuan D. Dang
(74) Attorney, Agent, or Firm—Kenneth H. Johnson

(57) ABSTRACT

A countercurrent process for the alkylation of aromatic materials with olefins which takes place in a multi-bed system. The aromatic material is in the liquid phase; the olefin in the gaseous phase; and the catalyst in the solid phase. The olefinic material is fed below the catalyst bed in the gaseous phase and aromatic is fed as a liquid phase above the catalyst bed under conditions of temperature and pressure to maintain the aromatic product in the liquid phase and the olefin in the vapor phase.

12 Claims, 1 Drawing Sheet

COUNTERCURRENT ALKYLATION PROCESS

This is a continuation, of application Ser. No. 09/445,783, filed May 12, 2000 now abandoned, which is a 371 of PCT/US97/12710, filed Jul. 16, 1997.

BACKGROUND OF THE INVENTION

1. Field of the Invention

The present invention relates to a process for the alkylation of organic aromatic materials in liquid phase which are reacted with olefins in the gaseous phase and the catalyst is in the solid phase. More particularly the invention relates to a countercurrent process.

2. Related Art

Chemical reactions between liquid and gaseous reactants often present difficulties in obtaining intimate contact between phases, especially when the reactions are catalyzed by porous solid catalysts. The three phases, solid, liquid and gas must all be contacted efficiently. In the typical reactor the solid catalyst is retained in a reactor and the reactants passed concurrently over the catalyst, usually downflow. Other common techniques for contacting liquid-gas mixtures with solid catalyst include slurry catalyst, ebulating beds and catalytic or reactive distillation.

Typically the alkylation of aromatic compounds with olefins has been carried out in the liquid phase. See for example U.S. Pat. Nos. 4,469,908; 4,891,458; 5,030,786; 5,081,323 and 5,196,623. More recently the alkylation of organic aromatic compounds with olefins has been carried out in a distillation column reactor. See for example U.S. Pat. Nos. 4,950,834; 5,019,669; 5,113,031; 5,215,725; and 5,243,115. In the distillation column reactor the catalyst is also acting as a distillation structure. The reaction mixture is boiling within the catalyst bed. Generally the olefin is fed as a gas below the catalyst bed and the aromatic compound is fed directly above or into the bed. The heat of reaction causes boil up and lighter materials are taken as overheads and the heavier materials are taken as bottoms. Generally the overheads contains the majority of unreacted aromatic compound and unreacted olefin. The bottoms contains the alkylated product and may also contain small amounts of the unreacted aromatic compound depending upon the efficiency of the stripping section in the distillation column reactor.

SUMMARY OF THE INVENTION

Briefly, the present invention is a process for the alkylation of organic aromatic compounds by countercurrent contact of a liquid organic aromatic compound and a gaseous olefin in a reactor containing a fixed bed of solid catalyst. The olefin is fed in the vapor phase below the catalyst bed and the organic aromatic compound is fed in the liquid phase above the catalyst bed.

The countercurrent operation provides a minimum residence time for the alkylation product in contact with the catalyst and thereby a greater selectivity towards the desired product. Because the vapor phase is a major carrier of the olefin a lower olefin concentration in the liquid phase results which provides for a much lower deactivation rate for the catalyst.

The process for the alkylation of organic aromatic compounds comprises the steps of:

(a) feeding a liquid stream containing an organic aromatic compound into a reactor above a bed of solid particulate aromatic alkylation catalyst;

(b) feeding a gaseous stream containing an olefin into the reactor below the bed of solid particulate catalyst;

(c) countercurrently contacting said organic aromatic compound with said olefin and said catalyst to react a portion of said organic aromatic compound with a portion of said olefin to produce an alkylated organic aromatic product under conditions to maintain organic aromatic compound and alkylated organic product in said liquid phase and olefins in said gaseous phase;

(d) withdrawing unreacted gaseous olefin from the reactor at a point above said bed of solid particulate catalyst; and (e) withdrawing unreacted organic aromatic compound and alkylated organic aromatic product from the reactor at a point below said bed of solid particulate catalyst.

DETAILED DESCRIPTION OF THE INVENTION

Figure 1:
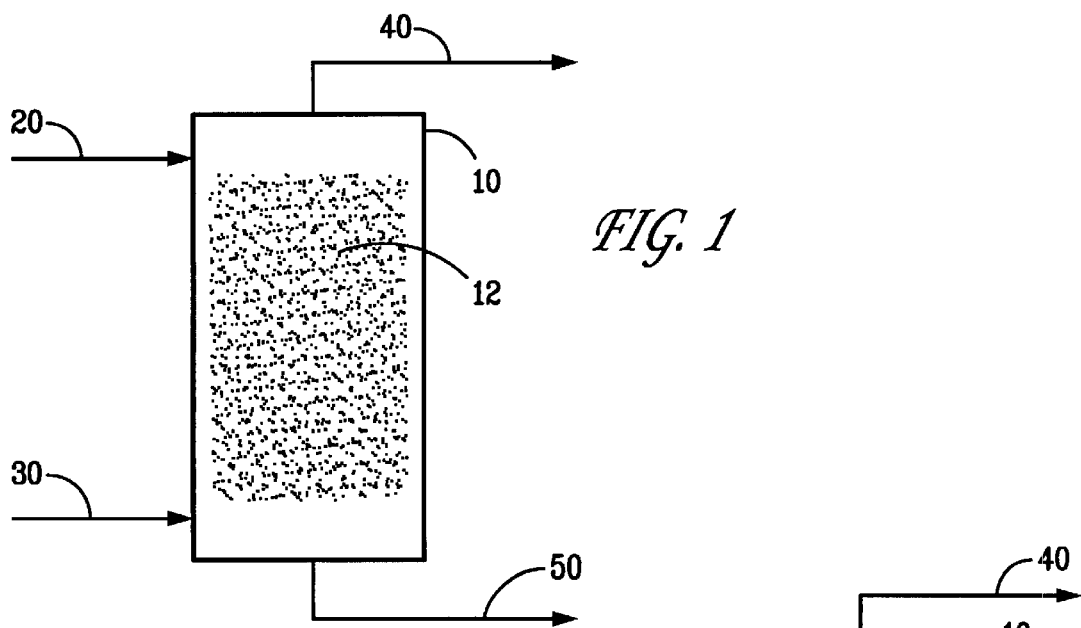
FIG. 1 is a flow diagram in schematic form of the basic process of the invention.

Countercurrent processes for contacting reactant fluids have several advantages. As the reactant gas rises upwardly from its point of introduction at the bottom of a vertical reactor below the catalyst bed, it contacts a lower concentration of reactive liquid components. At the point of entry the reactant gas has its highest concentration and depletion of the gaseous reactant as it rises will increase the relative concentration of inerts and/or by-product vapors. Likewise, the liquid reactant is more concentrated, and thus more reactive, at the upper end of the vertical reactor where it is introduced and where it contacts the depleted reactant vapor. Thus, the reactant concentration gradients for countercurrent multi-phase systems are opposing. In the present multi-phase reactor system the average gas-liquid volume ratio in the catalyst zone is about 1:4 to 10:1 under process conditions.

In order to maintain a desirable uniform flow of reactant streams through the fixed catalyst bed, adequate flow paths for liquid and gaseous phases must be provided. In a continuous process the ratio of reactant gas to liquid feedstock and the space velocity of reactants relative to catalyst must be carefully considered. Achievement of uniform vertical flow through a porous bed of solids can be obtained if the catalyst is properly distributed and shaped. The void volume in a reaction zone is a function of catalyst configuration and loading technique. While a densely packed bed of spherical solids may be employed to place a maximum amount of catalyst in a predetermined reactor volume, the low void fraction may interfere with fluid flow, especially where countercurrent flow of two phases is required. Advantageously, the catalyst bed has a high void volume, typically greater than one half of the bed. Void fractions from 0.5 to 0.9 can be achieved using loosely packed polylobes or cylindrical extrudates. Hollow ring-type supported catalysts, such as Raschig rings or the like, permit liquids to flow downwardly through the porous bed by gravity while the gas phase reactant rises through the denser liquid, forming dispersed bubbles which contact the wetted catalyst to enhance mass transfer and catalytic phenomena.

Catalyst size can vary widely within the inventive concept, depending upon process conditions and reactor structure. If a low space velocity or long residence in the catalytic reaction zone is permissible, small catalysts having an average maximum dimension of 1 to 5 mm may be employed. However, it is preferred to use larger sizes, e.g., 0.5–2 cm or more, especially when extrudates, rings, saddles or other contact materials are desired. Relatively small catalyst particles may be loaded randomly to assure uniformity and larger supported catalysts may be stacked in a geometric pattern to achieve optimum bed utilization.

Reactor configuration is an important consideration in the design of a continuously operating system. In its simplest form, a vertical cylindrical pressure vessel is provided with a catalyst retaining means and operatively connected for countercurrent gas/fluid flow. A typical vertical reactor having a catalyst bed length to effective diameter (L:D) ratio of about 1:1 to 20:1 is preferred. A single bed or a stacked series of beds may be retained within the same reactor shell. While a reactor of uniform horizontal cross section is disclosed herein, other non-uniform configurations, such as spherical reactors, tapered vessels, etc., may be employed.

The olefin used to alkylate aromatic compound may be ethylene, propylene, butenes, pentenes or hexenes or any mixture thereof. Also the olefin or olefins may be contained in a mixture of hydrocarbons or diluted by inert materials such as nitrogen, carbon monoxide oxygen, hydrogen or carbon dioxide. One useful olefin containing stream is the off gas from an FCCU olefin concentration plant. The FCCU off gas contains a variety of unrecovered olefins, however the preponderant olefinic compounds are ethylene, propylene (propenes) and butenes. The remainder of the gas is made up of various saturated hydrocarbons. Table I below gives a gas chromatography analysis of a typical waste gas useful in the present invention.

TABLE I

Typical Gas Analysis

| Component | wt. % |
|---|---|
| $C_1$ | 21.1 |
| $C_2^=$ | 11.1 |
| $C_2$ | 12.7 |
| $C_3^=$ | 30.6 |
| $C_3$ | 7.9 |
| $C_4^=$ | 0.4 |
| $C_4$ | 0.7 |
| $C_5^+$ | 0.1 |
| $N_2$ | 13.5 |
| $H_2$ | 1.7 |
| $CO_2$ | 0.3 |

The aromatic compound may be benzene, toluene or xylenes or any mixture thereof. The aromatics may be contained in a mixed hydrocarbon stream such as a light reformate stream from a catalytic reforming unit. The "reformed" product from a catalytic reforming process is commonly called reformate and is often separated into two fractions by conventional distillations and comprising a light reformate having a boiling range of circa 46–121° C. and a heavy reformate having a boiling range of circa 121–177° C. The aryl compounds in each fraction are thus dependent upon their boiling points. The lower boiling or lighter aryl compounds, e.g., benzene, toluene and xylenes, are contained in the light reformate and higher boiling aryl compounds are contained in the heavy reformate.

The preferred catalysts for the process are the acidic molecular sieves. Molecular sieves are porous crystalline, preferably three dimensional, alumina-silicates of the zeolite mineral group. The crystal skeleton is composed of silicon and aluminum atoms each surrounded by four oxygen atoms to form a small pyramid or tetrahedron (tetrahedral coordination). The term molecular sieve can be applied to both naturally occurring zeolites and synthetic zeolites. Naturally occurring zeolites have irregular pore size and are not generally considered as equivalent to synthetic zeolites. In the present invention, however, naturally occurring zeolites are acceptable so long as they are substantially pure. The balance of the present discussion shall be directed to the synthetic zeolites with the understanding that natural zeolites are considered equivalent thereto as indicated above, i.e., insofar as the natural zeolites are the functional equivalents to the synthetic zeolites.

Usually synthetic zeolites are prepared in the sodium form, that is, with a sodium cation in close proximity to each aluminum tetrahedron and balancing its charge. To date four principal types of molecular sieves have been reported, A, X, Y and L erionite, omega, beta and mordenite. The A types have relative small pore size. By the term pore size is meant the effective pore size (diameter) rather than the free pore size (diameter). Types X and Y have larger pore size (approximately 10 Å.) and differ as to the range of ratio of $Al_2O_3$ to $SiO_2$ as:

Type X—$Al_2O_3/2.0$–$3.0$ $SiO_2$
Type Y—$Al_2O_3/3.0$–$6.0$ $SiO_2$
Type L, beta and other types listed have still higher ratios of $SiO_2$ to $Al_2O_3$.

The molecular sieve catalysts employed in the present invention are the acid form molecular sieves or exhibit acidic characteristics. The acid form of the molecular sieves is commercially available, but also may be prepared by treating the molecular sieves with acid to exchange Na for hydrogen. Another method to produce the acid form is to treat the molecular sieve with decomposable cations (generally ammonium ions) to replace Na with the decomposable ions and thereafter to heat the molecular sieve to decompose the cation leaving the acid form. Generally the Na form molecular sieve is treated with soluble ammonium salts to remove the Na and thereafter the molecular sieve is heated to a temperature of about 350° C. to remove the ammonia. The removal of $Na^+$ ions with $NH^+_4$ is more easily carried out than with multivalent ions as described below and these catalysts are generally more active, but less stable to heat than the multivalent cation exchange forms. Molecular sieves, which have had their alkali metal reduced to low levels by partial treatment with $NH^+_4$ and partial multivalent metal cation exchange, possess increased activity and increased stability.

In addition to molecular sieves which are acidic according to the Bronsted Theory, those molecular sieves which exhibit acidic characteristics under the Lewis Theory, for example, calcium exchanged molecular sieves are suitable for the present reaction. By exchanging the univalent cations (e.g. $Na^+$) with multivalent cation, strong ionic activity is imparted. The ratio of $SiO_2:Al_2O_3$, valence and radius of the cation and the extent of exchange all affect the catalyst activity. In general activity increases with (1) increased $SiO_2:Al_2O_3$ ratio, (2) decreased cation radius and an increase in cation valence. The effect of replacing univalent ions (e.g. $Na^+$) with bivalent (e.g. $Ca^{++}$) is much greater than replacing the bivalent ions with cations of greater valence.

The various types of molecular sieves having reduced alkali metal content are characterized as the acid form molecular sieve and are all contemplated as useful in the present invention.

It would appear that the pore size within the crystal lattice may affect selectivity. According to one theory of molecular sieve catalytic activity, zeolite catalysis occurs primarily inside the uniform crystal cavities, consequently zeolitic catalyst activity depends on the number of aluminum atoms in the crystal and thus on the chemical composition of the crystal. Moreover, these catalytic sites are fixed within the rigid structure of the crystal, so that access to site can be altered by altering the structure of the crystal. The acid form molecular sieves are generally produced and available as particles in the range of <10 micron (powders) to 0.2 inch in diameter (beads).

The most preferred type of molecular sieves are the Y type or beta zeolites.

The present alkylation reaction can be carried out at sub-through super atmospheric pressure, e.g., 0.20 to 41 Kgs./sq.cm. The temperature will vary depending on the reactants and product. The reaction temperatures will generally be in the range of 50° C. to 500° C., preferably 70° C. to 500° C. for the molecular sieve catalyst. It must be born in mind that the reaction temperature and pressure must be adjusted to keep the aromatic compound and product in the liquid phase and the olefin in the vapor phase. Residence times of the olefin and aromatic can be adjusted to give the desired product mix but the liquid hourly space velocity (LHSV=volume of liquid/vol of catalyst/hr) of the liquid aromatic feed should be in the range of 0.5 to 10.0.

The mole ratio of organic aromatic compound to olefin may be in the range of 2 to 100:1, preferably 2 to 50:1 and more desirably about 2 to 10:1. The greater the excess of organic aromatic compound the more the selectivity to the monosubstituted product is improved.

Referring now to FIG. 1 there is shown a simplified flow diagram in schematic form of the basic form of the invention. The catalyst bed 12 is shown contained within a reactor 10. The aromatic compound containing feed is fed as a liquid above the bed 12 via flow line 20 and the olefin containing stream is fed below the bed 12 via flow line 30. Unreacted gases are removed via flow line 40 and liquid product along with unreacted aromatic compounds are removed via flow line 50.

Figure 2:
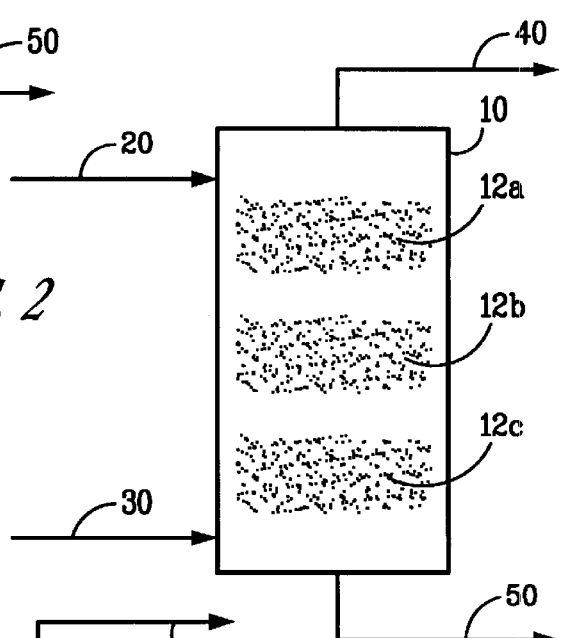
FIG. 2 is a flow diagram in schematic form of an alternate embodiment of the invention.

FIG. 2 shows a process similar to FIG. 1 except that there are multiple beds 12a, 12b and 12c of catalysts. The aromatic and olefin containing streams are fed as in FIG. 1. Although not shown, if the olefin is depleted to too great an extent in any one bed, fresh olefin may be added between the beds. Also the liquid from one bed may be removed and cooled before being passed to the next lower bed to remove the exothermic heat of reaction.

Figure 3:
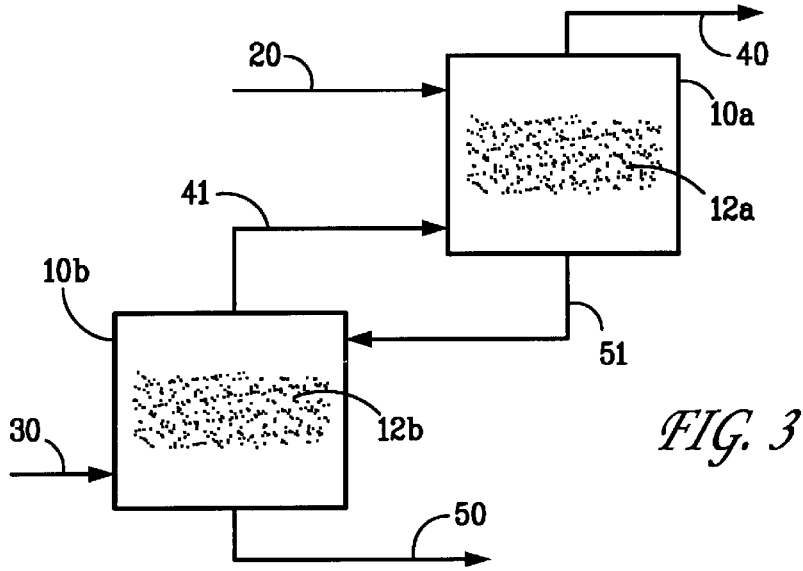
FIG. 3 is a flow diagram in schematic form of another embodiment of the invention.

Finally, FIG. 3 shows an arrangement wherein there is more than one reactor 10a and 10 each containing a bed of catalyst 12a and 12b respectively. The fresh aromatic containing stream is fed as a liquid into reactor 10a above catalyst bed 12a via flow line 20. The fresh olefin containing stream is fed below the catalyst bed 12b in reactor 10b via flow line 30. The liquid from reactor 10a is removed via flow line 51 and fed to reactor 10b above the catalyst bed 12b. The gaseous stream containing unreacted olefin is removed from reactor 10b via flow line 41 and fed to reactor 10a below the catalyst bed 12a. Again, if needed, fresh olefin may be fed between the reactors 10b and 10a and the liquid from reactor 10a may be cooled to remove the heat of reaction before feeding it to reactor 10b.

The invention claimed is:

1. A process for the alkylation of organic aromatic compounds comprising the steps of:
   (a) feeding a liquid stream containing an organic aromatic compound into a reactor at a point above a bed of solid particulate aromatic alkylation catalyst contained in said reactor;
   (b) feeding a gaseous stream containing an olefin into the reactor at a point below the bed of solid particulate aromatic alkylation catalyst;
   (c) countercurrently contacting said organic aromatic compound with said olefin and said solid particulate aromatic alkylation catalyst under conditions of temperature and pressure and an average gas-liquid volume ratio about 1:4 to 10:1 in said bed to react a portion of said organic aromatic compound with a portion of said olefin to produce an alkylated organic aromatic product and to maintain said organic aromatic compound and said alkylated organic aromatic product in said liquid phase and said olefins in said gaseous phase;
   (d) withdrawing unreacted gaseous olefin from the reactor at a point above said bed of solid particulate aromatic alkylation catalyst; and
   (e) withdrawing unreacted organic aromatic compound and alkylated organic aromatic product from the reactor at a point below said bed of solid particulate aromatic alkylation catalyst.

2. The process according to claim 1 wherein the pressure is adjusted at the reaction temperature to maintain substantially all of said organic aromatic compound and said alkylated organic aromatic product in the liquid phase.

3. The process according to claim 1 wherein said solid particulate aromatic alkylation catalyst comprises a zeolite.

4. The process according to claim 1 wherein said organic aromatic compound is selected from the group consisting of benzene, toluene, xylenes and mixtures thereof.

5. The process according to claim 1 wherein said olefin is selected from the group consisting of ethylene, propylene, butenes, pentenes, hexenes and mixtures thereof.

6. The process according to claim 1 wherein said organic aromatic compound is contained in a light reformate from a catalytic reforming unit.

7. The process according to claim 1 wherein said olefin is contained in an off gas from an FCCU olefin concentration unit.

8. The process according to claim 1 wherein said organic aromatic compound is contained in a light reformate from a catalytic reforming unit and said olefin is contained in an off gas from an FCCU olefin concentration unit.

9. The process according to claim 1 wherein there are at least two beds of solid particulate aromatic alkylation catalyst arranged in said reactor such that the beds are one above the other and the gaseous stream is fed below the lowest bed and the liquid stream is fed above the uppermost bed.

10. The process according to claim 1 wherein said solid particulate aromatic alkylation catalyst comprises beta zeolite.

11. A process for the alkylation of organic aromatic compounds comprising the steps of:
   (a) feeding a liquid light reformate stream containing organic aromatic compounds into a reactor at a point above a bed of solid particulate zeolite beta catalyst contained in said reactor;
   (b) feeding an off gas stream from an FCCU olefin concentration unit containing olefins into the reactor at a point below the bed of solid particulate zeolite beta catalyst;
   (c) countercurrently contacting said light reformate stream with said off gas stream and said solid particulate zeolite beta catalyst to react a portion of the organic aromatic compounds contained within said light reformate stream with a portion of the olefins contained within said off gas stream to produce alkylated organic aromatic products wherein the average gas-liquid volume ratio in said bed is about 1:4 to 10:1 under process conditions;

(d) withdrawing unreacted off gas from the reactor at a point above said bed of solid particulate zeolite beta catalyst; and (e) withdrawing unreacted light reformate and alkylated organic aromatic products from the reactor at a point below said bed of solid particulate zeolite beta catalyst.

12. A process for the alkylation of organic aromatic compounds comprising the steps of:

(a) feeding a liquid stream containing an organic aromatic compound into a reactor at a point above a bed of solid particulate catalyst;

(b) feeding a gaseous stream containing an olefin into the reactor at a point below the bed of solid particulate catalyst;

(c) countercurrently contacting said organic aromatic compound with said olefin and said solid particulate catalyst in a catalyst zone to react a portion of said organic aromatic compound with a portion of said olefin to produce an alkylated organic aromatic product and said average gas-liquid volume ratio in the catalyst zone is about 1:4 to 10:1 under process conditions;

(d) withdrawing unreacted gaseous olefin from the reactor at a point above said bed of solid particulate catalyst;

(e) withdrawing unreacted organic aromatic compound and alkylated organic aromatic product from the reactor at a point below said bed of solid particulate catalyst; and (f) adjusting the pressure within said reactor such that said aromatic containing stream and said alkylated organic aromatic product remain substantially in the liquid phase and said olefin containing stream remains substantially in the vapor phase.

* * * * *